US00PP26593P2

(12) United States Plant Patent
van Noort

(10) Patent No.: US PP26,593 P2
(45) Date of Patent: Apr. 5, 2016

(54) ***ECHINACEA* PLANT NAMED 'SENSATION PINK'**

(50) Latin Name: ***Echinacea* hybrid**
Varietal Denomination: Sensation Pink

(71) Applicant: Marco van Noort, Warmond (NL)

(72) Inventor: Marco van Noort, Warmond (NL)

(73) Assignee: Marco van Noort Breeding BV, Warmond (NL)

( * ) Notice: Subject to any disclaimer, the term of this patent is extended or adjusted under 35 U.S.C. 154(b) by 310 days.

(21) Appl. No.: 13/999,159

(22) Filed: Jan. 17, 2014

(51) Int. Cl.
*A01H 5/02* (2006.01)

(52) U.S. Cl.
USPC ..... Plt./428

(58) Field of Classification Search
USPC ..... Plt./428
See application file for complete search history.

*Primary Examiner* — June Hwu
(74) *Attorney, Agent, or Firm* — Penny J. Aguirre

(57) ABSTRACT

A new cultivar of hybrid *Echinacea* named 'Sensation Pink', that is characterized by its healthy, upright, and consistently shaped plant habit, its densely pubescent stems that are dark gray-orange in color, its inflorescences with ray florets that are bright pink in color and held at a consistent angle to the disk, and its flowering at a young age requiring only 4.5 months to develop into a branched flowering plant from tissue culture.

2 Drawing Sheets

Botanical classification: *Echinacea* hybrid.
Variety denomination: 'Sensation Pink'.

BACKGROUND OF THE INVENTION

The present invention relates to a new and distinct cultivar of *Echinacea* of hybrid origin and will be referred to hereafter by its cultivar name 'Sensation Pink'. 'Sensation Pink' is an herbaceous perennial grown for landscape and container use.

The new invention arose from an ongoing controlled breeding program in Warmond, The Netherlands. The objective of the breeding program is to develop cultivars of *Echinacea* with superior health and rich-flowering habits.

The Inventor made a controlled cross in July 2008 in his test garden in Warmond, The Netherlands between an unnamed proprietary seedling of *Echinacea purpurea* from the Inventors breeding program as the female parent, and an unnamed proprietary seedling of *Echinacea angustifolia* as the male parent. 'Sensation Pink' was selected in August 2011 as a single unique plant amongst the resulting seedlings from the above cross.

Asexual propagation of the new cultivar was first accomplished by tissue culture in Warmond, The Netherlands in October 2012 by the Inventor. Asexual propagation by tissue culture and division has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Sensation Pink' as unique cultivar of *Echinacea*.

1. 'Sensation Pink' exhibits a healthy, upright, and consistently shaped plant habit.
2. 'Sensation Pink' exhibits densely pubescent stems that are dark gray-orange in color.

3. 'Sensation Pink' exhibits inflorescences with ray florets that are bright pink in color and held at a consistent angle to the disk.
4. 'Sensation Pink' exhibits flowering at a young age; requiring only 4.5 months to develop into a branched flowering plant from tissue culture.

The female parent of 'Sensation Pink', a proprietary seedling of *Echinacea purpurea* from the Inventor's breeding program, differs from 'Sensation Pink' in having a less compact plant habit, in being much less densely branched, in being less floriferous, in having stems that are not densely pubescent or dark gray-orange in color, and in having ray florets that are lighter pink in color. The male parent of 'Sensation Pink', a proprietary seedling of *Echinacea angustifolia* from the Inventor's breeding program, differs from 'Sensation Pink' in having ray florets that are more prone to drooping and less intensely colored, in having stems that are not densely pubescent or dark gray-orange colored, and in being a weaker plant. 'Sensation Pink' can be most closely compared to the *Echinacea* cultivars 'Magnus' (not patented) and 'Purple Emperor' (U.S. Plant Pat. No. 24,459). 'Magnus' differs from 'Sensation Pink' in having a less compact plant habit, a taller plant height, in having lighter, less intensely colored flowers, and in having stems that are not densely pubescent or dark gray-orange colored. 'Purple Emperor' is similar to 'Sensation Pink' in plant habit and plant height. 'Purple Emperor' differs from 'Sensation Pink' in having lighter, less intensely colored flowers, in having stems that are not densely pubescent or dark gray-orange colored, and in having ray florets that are not placed at different angles from the disk.

BRIEF DESCRIPTION OF THE DRAWING

The accompanying colored photographs illustrate the overall appearance and distinct characteristics of the new *Echinacea*. The photographs were taken of one-year-old plants of the new cultivar as field grown in Warmond, The Netherlands.

The photograph in FIG. 1 illustrates the overall habit and appearance of a plant of 'Sensation Pink'.

Figure 1:
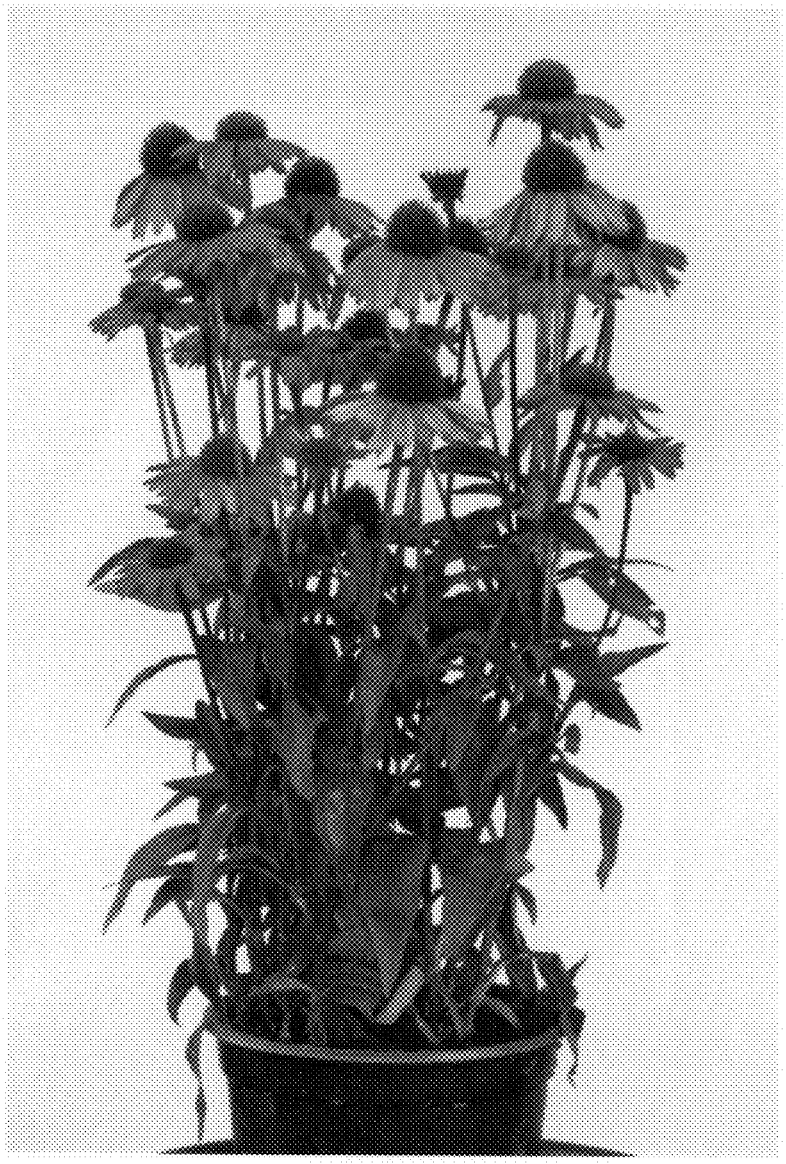
Figure 2:
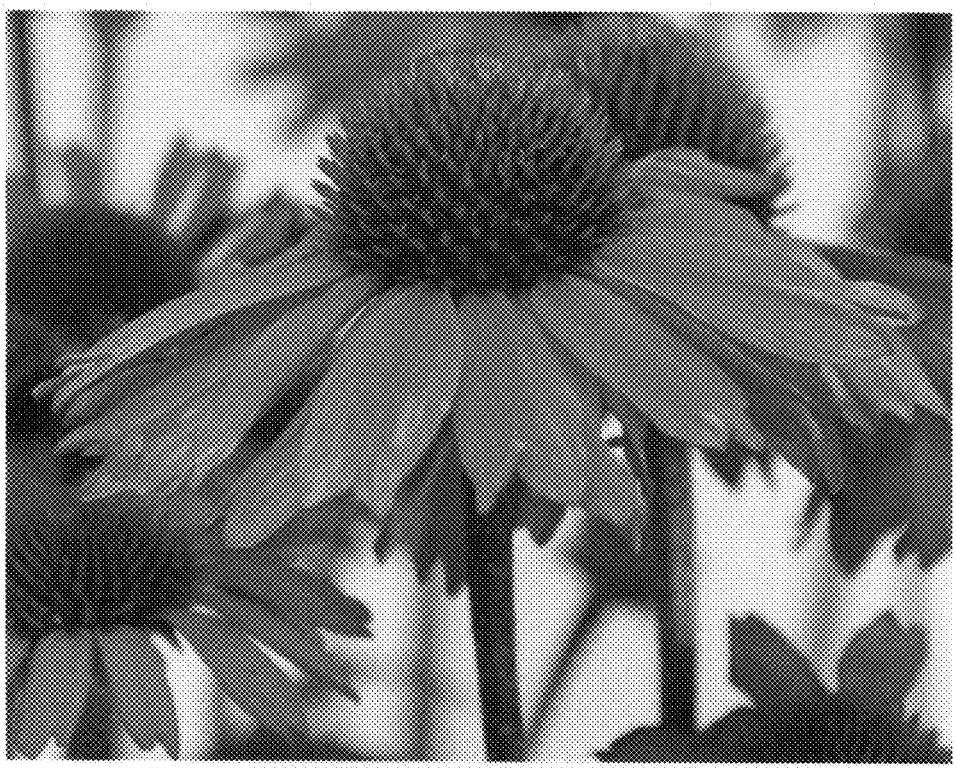

The photograph in FIG. 2 provides a close-up view of an inflorescence of 'Sensation Pink'.

Figure 3:
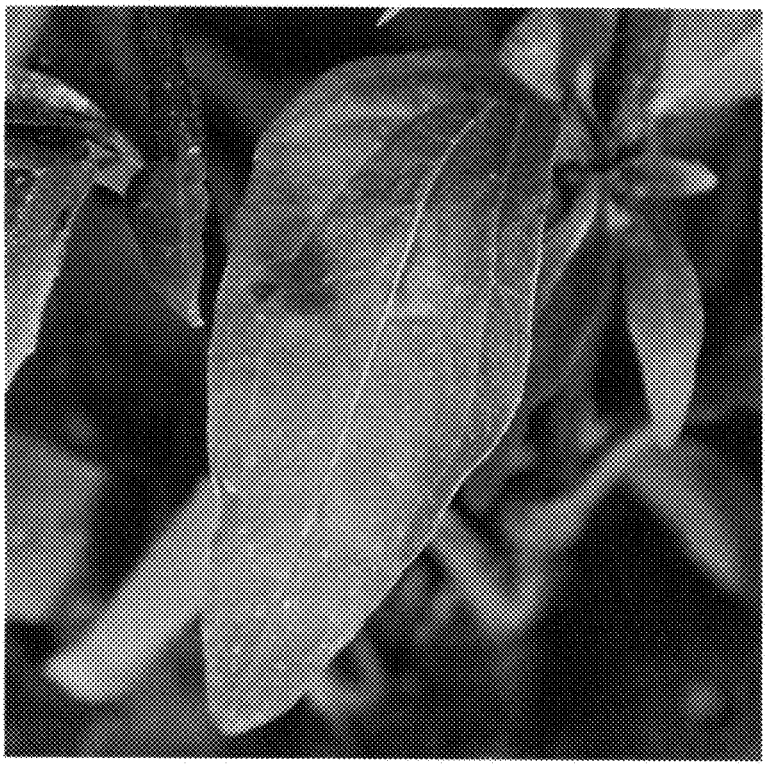

The photograph in FIG. 3 provides a close-up view of a leaf of 'Sensation Pink'.

The colors in the photographs are as close as possible with the photographic and printing technology utilized and the color values cited in the detailed botanical description accurately describe the colors of the new *Echinacea.*

BOTANICAL DESCRIPTION OF THE PLANT

The following is a detailed description of one-year-old plants of the new cultivar as field grown outdoors in Warmond, The Netherlands (place in a container for the photographs). The plants were grown under average day temperatures of 18° to 32° C. and average night temperatures of 8° to 20° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Continuously from early July to late September in The Netherlands.

*Plant habit.*—Herbaceous perennial, upright, consistent.

*Height and spread.*—Reaches about 50 cm in height 45 cm in spread.

*Hardiness.*—At least in U.S.D.A. Zone 3.

*Diseases resistance.*—Not more susceptible to pests/diseases than other *Echinacea* varieties.

*Root description.*—Fibrous and fine.

*Propagation.*—Tissue culture and division.

*Growth rate.*—Moderately vigorous.

Stem description:

*Shape.*—Rounded.

*Stem color.*—165A, tinged towards the distal end 199A.

*Stem size.*—An average of 4 mm in diameter and 26 cm in length (from base of plant to base of uppermost leaf).

*Stem strength.*—Strong.

*Stem aspect.*—Stems grow in an average angle of 80° from the base (0°=horizontal).

*Stem surface.*—Rough to touch and densely covered with very short strigose hairs about 1.5 mm in length and NN155D in color.

*Stem number.*—Average of 17 main stems.

*Internode length.*—Average of 3.1 cm in length.

*Branching.*—Flowering stems emerge from base.

Foliage description:

*Leaf shape.*—Narrow ovate.

*Leaf division.*—Simple.

*Leaf base.*—Attenuate.

*Leaf apex.*—Acute.

*Leaf venation.*—Pinnate, color: upper surface; 146C, lower surface; 145B to 145C.

*Leaf margins.*—Entire, slightly undulate.

*Leaf attachment.*—Petiolate.

*Leaf arrangement.*—Alternate.

*Leaf size.*—Average of 8.8 cm in length and 3.5 cm in width.

*Leaf color.*—Young upper surface; 137B, young lower surface; 143C, mature upper surface; NN137A, mature lower surface; NN137B.

*Leaf surface.*—Upper surface is slightly glossy, lower surface is moderately glossy, both surfaces are moderately covered with short strigose hairs an average of 0.5 mm in length and NN155D in color.

*Petioles.*—V-shaped, 2.1 cm in length and 5 mm in diameter, color upper surface 146D with margins are 137B, color lower surface 145A with margins 137B to 137C, both surfaces smooth and covered with very short strigose hairs an average 0.5 mm in length and NN155D in color.

Flower description:

*Type.*—Terminal capitulum consisting of single ray florets surrounding disc florets.

*Capitulum number.*—An average of 1 per stem.

*Lastingness of inflorescence.*—About 2 weeks.

*Capitulum size.*—Matures to about 4.8 cm in height and 8.4 cm in diameter, disc diameter is 3.3 cm.

*Fragrance.*—None.

*Involucral bracts or phyllary.*—About 48 arranged in 3 overlapping rows, average of 9 mm in length and 3 mm in width, cuneate base, acute apex, entire margin, narrowly ovate to ovate in shape, color upper surface N137B, color lower surface 137B, upper surface is smooth and dull, lower surface is dull with margins moderately covered with very short hairs an average of 0.5 mm in length and 157D in color.

*Buds.*—Flattened globular in shape, immature ray florets near vertical (upright), an average of 1.7 cm in length and 3 cm in diameter, 175A in color, immature ray florets 185A to 185B in color.

*Peduncle.*—Strong, terminal is an average of 16.7 cm in length (from uppermost leaf to base of inflorescence) and 3 mm in diameter, held upright with secondary peduncles held at an average angle of 40° to vertical, color 165A and tinged 199A, surface is moderately covered with short strigose hairs up to 0.5 mm in length and NN155D in color.

*Ray florets.*—Rotate, average of 20 per inflorescence, oblanceolate in shape, upper surface dull, smooth and slightly ribbed lengthways, lower surface smooth, slightly glossy and moderately ribbed lengthways, about 4 cm in length and 1.2 cm in width, emarginate to cleft apex, cuneate base, entire margin, slightly drooping in an average angle of about 20° downward from horizontal (consistent to all florets), color of upper surface when opening; between N57A and 61B, color of lower surface when opening; 60C, color of upper surface when fully open; 61B, color of lower surface when fully open; 60C, upper surface fading to 64A and 64B, lower surface fading to 60C.

*Disk flowers (bisexual).*—Numerous, average of 250, arranged spirally on disc, apex is acute on upper 15% free portion, fused (tubular) base, entire margin, average of 7 mm in length and 2 mm in width, upper lower surfaces are smooth and glossy, color when opening and fully open upper and lower surfaces; 144A with base 151D.

*Disk spines*.—Average of 250, acicular in shape, acute apex, attenuate base, smooth and glossy surface, color is 53A at apex, 26B in mid region and 143B at base.

*Receptacle*.—Triangular in shape, an average of 1.1 cm in height and 8 mm in diameter, and 155D in color.

Reproductive organs (present on disk florets only):

*Gynoecium*.—Pistil; 1, 7.5 mm in length, styles; about 6 mm in length and 145A in color, stigmas; unequal decurrent and 179A in color, ovaries; 145D in color.

*Androcoecium*.—Stamens; 5, filaments; 3 mm in length and 145D in color, anthers; linear in shape, about 3 mm in length and 200A in color, pollen; moderate in quantity and 17A in color.

*Fruit/seed*.—No seed production has been observed.

It is claimed:

1. A new and distinct cultivar of *Echinacea* plant named 'Sensation Pink' as herein illustrated and described.

* * * * *